United States Patent [19]

Bader et al.

[11] Patent Number: 5,488,128
[45] Date of Patent: Jan. 30, 1996

[54] MONOMER FOR HIGH REFRACTIVE INDEX PLASTICS

[75] Inventors: Martina Bader, Griesheim; Volker Kerscher, Reinheim, both of Germany

[73] Assignee: Roehm GmbH Chemische Fabrik, Darmstadt, Germany

[21] Appl. No.: 134,738

[22] Filed: Oct. 12, 1993

[30] Foreign Application Priority Data

Oct. 10, 1992 [DE] Germany .......................... 42 34 253.8

[51] Int. Cl.$^6$ .................................................. C07C 327/36
[52] U.S. Cl. .................... 558/251; 558/249; 558/250
[58] Field of Search ............................................... 558/251

[56] References Cited

U.S. PATENT DOCUMENTS 4,810,812  3/1989  Matsuda et al. .................... 558/251

*Primary Examiner*—José G. Dees
*Assistant Examiner*—Dwayne C. Jones
*Attorney, Agent, or Firm*—Oblon, Spivak, McClelland, Maier, & Neustadt

[57] ABSTRACT

The invention relates to a thio(meth)acrylic acid bisester of formula I

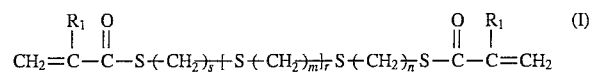

where
  $R_1$ represents hydrogen or methyl;
  r represents the number 0 or 1; and
  s, m, and n independently represent an integer from 2 to 6, with the proviso that
when r=0, s+n>4; and
when r=1, s+m+n>6 useful as or monomer for high refractive index plastics.

6 Claims, No Drawings

MONOMER FOR HIGH REFRACTIVE INDEX PLASTICS

FIELD OF THE INVENTION

The invention relates to a monomer for high refractive index plastics in the group of the thio(meth)acrylic acid bisesters.

DISCUSSION OF THE BACKGROUND

Sulfur-containing monomers are good candidates for producing high refractive index optical materials, because the ready polarizability of the sulfur produces a strong interaction between the material and incident light, resulting in a high refractive index. Aliphatic thioether (meth)acrylates, monofunctional or bifunctional, such as comprise, e.g., the principal claimed matter of DE-OS 38 38 350, have an upper limit on their sulfur content (namely, according to the examples, 27 wt. % sulfur, for acetal-free structures), and accordingly the index of refraction of a polymer is <1.58.

Aromatic structural elements also contribute to the raising of the refractive index, but they also contribute to increased dispersion. Low dispersion is desirable, in order to minimize the chromatic aberration of the polymer.

A higher sulfur content can be achieved, even with relatively simple structures, by means of esters of thio(meth)acrylic acid. Thus, the alkyl dithiomethacrylates described in EP-A 273,661 have a sulfur content of up to 39 wt. %. However, the ethyl sulfide partial structure (thioether-thiomethacrylate) causes problems during the production process—the yields in producing and purifying the dimercaptans used to prepare the dimethacrylates are unsatisfactory, because 1,4-dithiane forms readily, tending to form via decomposition of the higher dimercaptans. It does not appear possible to avoid purifying the mercaptan to be used as the starting product, however, because it is very difficult to purify the dithio(meth)acrylate products in an industrial process, in view of their high boiling points; i.e. at the stage at which the end product is produced, it is no longer possible to remove by-products and decomposition products.

Thus there is a continuing need for monomers with high sulfur content which are easily obtained or produced, which are colorless, and which preferably are a liquid at room temperature.

It has been discovered, in connection with the present invention, that by the inclusion of alkylidene bridges with more than two C atoms between the sulfur atoms, dimercaptans can be produced as pure products which can then be reacted to form the corresponding bisthio(meth)acrylates.

SUMMARY OF THE INVENTION

Thus the invention relates to a thio(meth)acrylic acid bisester of general formula I $$CH_2=\underset{R_1}{C}-\underset{O}{\overset{O}{C}}-S-(CH_2)_s-[S-(CH_2)_m]_r-S-(CH_2)_n-S-\underset{O}{\overset{O}{C}}-\underset{R_1}{C}=CH_2 \quad (I)$$

where $R_1$ represents hydrogen or methyl;
r represents the number 0 or 1; and
s, m, and n independently represent an integer from 2 to 6, with the proviso that
when r=0, s+n>4; and
when r=1, s+m+n>6.

The result of abandoning ethyl bridges as the sole repeating unit is that a smaller amount of byproducts attributable to cyclization are formed, because the tendency for the formation of medium sized rings (i.e., with 7–9 C atoms) is much less than the tendency to formation of the six-membered ring of dithiane. It has also been found that liquid dimercaptans are more advantageous as starting materials for the production process. When thio groups are introduced by way of thiourea, with solid dimercaptans separation problems result, and thereby an increased consumption of solvent. Thus, 1,2-bis(2-mercaptoethylthio)ethane is a solid, whereas 1,3-bis(2-mercaptoethylthio)propane is a liquid. Noteworthy thio(meth)acrylic acid bisesters are 1,3-bis(2-methacryloylthioethylthio)propane (compound of formula I with r=1, m=3, and s, n=2) and 1,6-bis(methacryloylthio)-3-thiahexane (compound of formula I with r=0, s=3, and n=2.

The invention also relates to a method of manufacturing the compounds of general formula I wherein one reacts i) a dithiol of general formula II $$MS-(CH_2)_s-[S-(CH_2)_m]_r-S-(CH_2)_n-SM \quad (II)$$

where r, s, m, and n are as defined above; and
M represents hydrogen or a metal cation, preferably an alkali cation;
with ii) at least two times the molar amount of a (meth)acrylic acid derivative of formula III $$CH_2=\underset{R_1'}{C}-\underset{O}{\overset{O}{C}}-X \quad (III)$$

where X represents $$-O-\underset{O}{\overset{O}{C}}-\underset{R_1'}{C}=CH_2$$

or Cl; and
$R'_1$ represents hydrogen or methyl.

DETAILED DESCRIPTION OF THE PREFERRED EMBODIMENTS

Advantageously, the (meth)acrylic acid anhydride or -chloride is reacted in a suitable inert, and preferably water-immiscible, solvent L; e.g., an ether such as methyl-t-butyl ether (MTBE), or an aromatic solvent such as toluene or xylene.

Preferably the dithiol of formula II is employed in an aqueous alkaline solution, so that the acid HX (if M is H) formed during the reaction will be neutralized.

The dithiols of general formula II may be obtained by methods which are per se known. The method will be described with reference to the example of 3,7-dithianonane-1,9-dithiol. First, 2-mercaptoethanol is dissolved in an ethanolic aqueous sodium hydroxide solution, preferably under an inert protective gas such as nitrogen or argon, and under cooling with ice, and one half the molar amount of 1,3-dibromopropane is added dropwise under stirring at c. 50° C. After a few hours of reaction time (suggested time 6 hr), the salt which is formed is filtered out, and an inert, water-immiscible solvent, e.g. methylene chloride, is added to the raw solution, followed by a second filtration. Preferably, the 3,7-dithianonane-1,9-dithiol which is formed is further purified by fractional distillation under high vacuum. The resulting diol is heated 8 hr under reflux with thiourea in a molar ratio of ca. 1 mol diol:2 mol thiourea, in concentrated HCl (i.e., 37% aqueous HCl), under nitrogen. Then aqueous alkali, preferably KOH solution, is added under ice cooling, and the mixture is again heated under reflux, c. 3 hr. The organic phase is separated out from the cooled reaction mixture, and the aqueous phase is acidified and is extracted with an inert water-insoluble solvent, e.g. MTBE. The organic phases are combined. After drying, and evaporation of the solvent, the dithiol is recovered as a colorless liquid by high vacuum distillation.

Manufacture of thio(meth)acrylic acid bisesters of formula I:

The manufacture of the starting compounds of formula III has long been known (see Rauch-Puntigam, H., and Voelker, Th., 1967, "Acryl- und Methacrylverbindungen", pub. Springer-Verlag). Preferably the compound of formula III, which particularly may be (meth)acrylic acid anhydride, is employed in a certain molar excess, e.g. a factor of 0.05–0.5 above the stoichiometric amount; advantageously a polymerization inhibitor (per se known) is employed for stabilization, from the class of sterically hindered phenols, e.g. 4-methyl-2,6-di-t-butylphenol, 2,4-dimethyl-6-t-butylphenol, or t-butylpyrocatechol; or quinone compounds such as hydroquinone monomethyl ether (see Gaechter, R., and Mueller, H., 1979, "Taschenbuch der Kunststoff-Additive", pub. Hanser-Verlag).

The reaction is carried out by adding dropwise the solution of the compound of formula II in aqueous alkali, e.g. 10% sodium hydroxide (c. 0.1 mol per 100 ml), with ice cooling, under stirring, to a solution of the compound of formula III, preferably a (meth)acrylic acid anhydride, in the inert solvent L (e.g. MTBE) (c. 1 g solute per 6–7 ml solvent), advantageously at 15°–20° C. Stirring is continued for several hours after completion of the dropwise addition, at elevated temperature, e.g. 3 hr at 45° C. After separation out of the organic phase and (advantageously) washing the organic phase with water, the organic phase is dried with a suitable drying agent, e.g. sodium sulfate, and the solvent is removed by evaporation. In this way, the compound of formula I is obtained directly.

Advantageous Properties and Applications

The inventive monomer of formula I may be polymerized by radical polymerization (see Rauch-Puntigam, H., and Voelker, Th., loc. cit.) e.g. to produce high refractive index plastics (preferably >1.59, more preferably >1.62) which are transparent and colorless (or colored if required).

Such plastics are suitable for numerous optical devices and articles, e.g. lenses, prisms, eyeglass lenses, etc.

Having generally described this invention, a further understanding can be obtained by reference to certain specific examples which are provided herein for purposes of illustration only and are not intended to be limiting unless otherwise specified.

The following Examples serve to illustrate the invention. In the Examples, the index of refraction and the Abbe number are obtained with the aid of an Abbe refractometer. The Abbe number can be determined with the aid of dispersion tables (see DIN 53 491; 1978 "Ullmanns Encyclopaedie der technischen Chemie", 4th Ed., Vol 15, pub. Verlag Chemie, p. 368).

EXAMPLES

Example 1

Production of 1,3-bis(2-methacryloylthioethylthio)propane (formula I with $R_1=CH_3$, r=1, m=3, and s, n=2)

A solution of 0.44 mol 3,7-dithianonane-1,9-dithiol in 400 mL 10% sodium hydroxide solution, prepared with ice cooling, was added dropwise at 15°–20° C. under stirring to a solution of 150 g methacrylic acid anhydride in 950 ml MTBE in the presence of 3,000 ppm 4-methyl-2,6-di-t-butylphenol. After completion of the dropwise addition, the mixture was stirred an additional 3 hr at 45° C., and the organic phase was separated out in a separatory funnel and washed with water. Following drying with sodium sulfate and removal of the solvent on a rotary evaporator, 150 g of the methacrylate ester of formula I (94% of theoretical) was obtained.

Example 2

Preparation of 3,7-dithiononane-1,9-dithiol (a) Preparation of 3,7-dithiononane-1,9-dithiol 312 g (4 mol) 2-mercaptoethanol in ethanolic sodium hydroxide solution (161 g sodium hydroxide in 2.2 l ethanol) was charged to the reactor, with ice cooling and under a nitrogen atmosphere. 2 mol Dibromopropane was added dropwise at 50° C. After 6 hr reaction time, the salt which formed was filtered out, 600 ml methylene chloride was added to the unrefined solution, and the mixture was filtered again. Following fractional distillation, 328 g 2,7-dithiononane- 1,9-diol was obtained (84% of theoretical, boiling point 167°–169° C. at 2 mbar, purity by GC-MS analysis >95%).

(b) Production of 3,7-dithiononane-1,9-dithiol 140.5 g (0.72 mol) of the diol 2 (a), 120 g thiourea, and 376 g concentrated HCl (37 wt. % aqueous) were heated 6 hr at reflux under nitrogen, on a water bath. Then 268 g KOH in 1.7 l water was added, under ice cooling, and the mixture was heated 3 hr under reflux. Following cooling, the reaction mixture was separated in a separatory funnel, and the aqueous phase was acidified with dilute HCl and then extracted with MTBE. The combined organic phases were dried with sodium sulfate and then were distilled.

136 g of the colorless dithiol was obtained (73% of theoretical, boiling point 140°–150° C. at 0.1 mbar).

Example 3

Production of 3-thiohexane-1,6-dithiol (a) Preparation of 3-thiohexane-1,6-diol 0.68 g azobis(isobutyronitrile) was added to 390 g (5 mol) 2-mercaptoethanol, under stirring and passage of nitrogen, and the mixture was heated 1 hr at 60° C. 290 g (5 mol) Allyl alcohol was added dropwise over 4 hr, while maintaining the 60° C. temperature. After completion of the dropwise addition and subsidence of the exothermic reaction, the mixture was allowed to react an additional 1.5 hr at 75° C., followed by distillation of the raw product in vacuum (b.p. 118°–121° C. at 0.2–0.4 mbar). 588 g of 3-thiohexane-1,6-diol was obtained, as a light-yellow liquid (86% of theoretical, purity >95% by GC analysis).

(b) Preparation of 3-thiohexane-1,6-dithiol

A mixture of 136 g (1 mol) 3-thiohexane-1,6-diol from 3(a), 168 g (2.2 mol) thiourea, and 0.525 l (5.4 mol) concentrated HCl (37 wt. % aqueous) was heated 16 hr under reflux, with stirring and passage of nitrogen. After cooling, a solution of 333 g (5.9 mol) KOH in 1.9 l water was added dropwise with cooling at c. 20° C. over a period of 1–1.5 hr, following which the mixture was heated 3 hr at reflux. The cooled reaction mixture was extracted with MTBE. After the extractant was removed on a rotary evaporator, the unrefined mercaptan was fractionally distilled (b.p. 92°–96° C. at 0.1–0.3 mbar).

The result was 92 g of colorless 3-thiohexane-1,6-dithiol (55% of theoretical, purity >97% by GC analysis).

Example 4

Production of 1,6-bis(methacryloylthio)-3-thiohexane

A solution of 252 g (1.5 mol) 3-thiohexane-1,6-dithiol and 144 g (3.6 mol) sodium hydroxide in 1.4 l water was added dropwise to a solution of 500 g (3.3 mol) methacrylic acid anhydride and 500 mg 2,5-di-t-butyl-4-methylphenol in 1.6 l MTBE at 15°–20° C., with passage of air, stirring, and cooling. The mixture was then allowed to react 3 hr at 40° C. Following cooling, the organic phase was separated out in a separatory funnel and washed with 3×0.6 l water. After drying with sodium sulfate and removal of the solvent on a rotary evaporator with addition of 750 ppm 2,5-di-t-butyl-4-methylphenol, 415 g 1,6-bis(methacryloylthio)-3-thiohexane was obtained, as an oily liquid (92% of theoretical yield).

Example 5

Polymer of 1,3-bis(2-methacryloylthioethylthio)propane 118 mg azobis(isobutyronitrile) was added to 32 g 1,3-bis(2-methacryloylthioethylthio)propane produced according to Example 1. The mixture was charged between two glass plates (c. 90×120×3 mm) and was polymerized in a water bath over a period of 28 hr, with a temperature schedule of 40°–90° C. The clear, hard plastic plate had index of refraction 1.6219 and an Abbe number of 38.6.

Example 6

Copolymer of methyl methacrylate and 1,6-bis(methacryloylthio)-3-thiohexane 63 mg azobis(isobutyronitrile) was added to a monomer mixture comprising 28 g 1,6-bis(methacryloylthio)-3-thiohexane and 3.1 g methyl methacrylate, and polymerization was carried out as above. The clear, hard plastic plate had an index of refraction of 1.5998 and an Abbe number of 41.1.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by letter patent of the United States is:

1. A thio(meth)acrylic acid bisester of the formula I

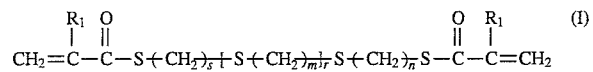

(I)

wherein $R_1$ represents hydrogen or methyl;

r represents the number 0 or 1; and s, m, and n each independently represents an integer from 2 to 6, with the proviso that when r=0, s+n>4; and when r=1, s+m+n>6.

2. The thio(meth)acrylic acid bisester of claim 1, wherein r=0, s=3 and n=2.

3. The thio(meth)acrylic acid bisester of claim 1, wherein r=1, m=3, and s, n=2.

4. 1,3-bis(2-methacryloylthioethylthio) propane.

5. 1,6-bis(methacryloylthio)-3-thiohexane.

6. A method of producing a thio(meth)acrylic acid bisester of the formula I

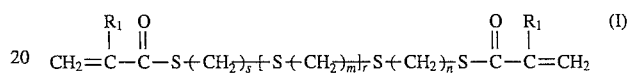

(I)

wherein $R_1$ represents hydrogen or methyl;

r represents the number 0 or 1; and s, m, and n each independently represent an integer from 2 to 6, with the proviso that when r=0, s+n>4; and when r=1, s+m+n>6;

comprising reacting i) a dithiol of the formula II

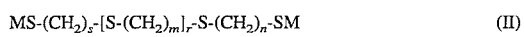

(II)

where r, s, m, and n are each independently defined above; and

M represents hydrogen or a metal cation; with ii) at least two times the molar amount of a (meth)acrylic acid derivative of formula III

(III)

where X represents

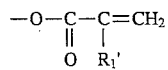

and $R'_1$ represents hydrogen or methyl.

* * * * *